(12) United States Patent
Harvey

(10) Patent No.: US 7,964,022 B2
(45) Date of Patent: Jun. 21, 2011

(54) METHOD AND APPARATUS FOR SELECTIVE CAPTURE OF GAS PHASE ANALYTES USING METAL β-DIKETONATE POLYMERS

(75) Inventor: Scott D. Harvey, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 276 days.

(21) Appl. No.: 12/367,413

(22) Filed: Feb. 6, 2009

(65) Prior Publication Data

US 2010/0058924 A1 Mar. 11, 2010

(51) Int. Cl.
*G01N 33/00* (2006.01)
(52) U.S. Cl. ........... 95/88; 95/128; 96/413; 73/31.01
(58) Field of Classification Search ............. 95/82, 88, 95/90, 128, 129, 141; 96/101, 108, 154, 96/413; 73/23.2, 23.35, 23.41, 31.01, 31.02, 73/863.23
See application file for complete search history.

(56) References Cited

U.S. PATENT DOCUMENTS

| | | | |
|---|---|---|---|
| 6,749,811 B2 | 6/2004 | Murray | |
| 2003/0178607 A1* | 9/2003 | Swager et al. | 252/582 |
| 2006/0073607 A1 | 4/2006 | Rose et al. | |
| 2006/0127929 A1* | 6/2006 | Swager et al. | 435/6 |

OTHER PUBLICATIONS

Harvey, Scott D., "Molecularly imprinted polymers for selective analysis of chemical warfare surrogate and nuclear signature compounds in complex matrices", 2005, Wiley-VCH, J. Sep Sci 28, 1221-1230.*
Harvey, Scott D. and Wenzel, Thomas J., Selective gas-phase capture of explosives on metal β-diketonate polymers, Journal of Chromatography A, 1192 (2008) pp. 212-217.

* cited by examiner

*Primary Examiner* — Frank M Lawrence
(74) *Attorney, Agent, or Firm* — James D. Matheson

(57) ABSTRACT

A process and sensor device are disclosed that employ metal β-diketonate polymers to selectively capture gas-phase explosives and weaponized chemical agents in a sampling area or volume. The metal β-diketonate polymers can be applied to surfaces in various analytical formats for detection of: improvised explosive devices, unexploded ordinance, munitions hidden in cargo holds, explosives, and chemical weapons in public areas.

15 Claims, 6 Drawing Sheets

Chemical structure of Cu(dihed) polymer where R=$-CF_2CF_2CF_3$.

TNT 2,6-DNT

4-NT

TATP

DMDNB

BN

PN

Exemplary Explosives Selectively Captured by the Invention.

US 7,964,022 B2

METHOD AND APPARATUS FOR SELECTIVE CAPTURE OF GAS PHASE ANALYTES USING METAL β-DIKETONATE POLYMERS

This invention was made with Government support under Contract DE-AC05-76RLO1830 awarded by the U.S. Department of Energy. The Government has certain rights in the invention.

FIELD OF THE INVENTION

The present invention relates generally to polymer compositions for selective adsorption. More particularly, the invention relates to a process that employs metal β-diketonate polymers for selective capture of gas-phase explosives and weaponized chemical agents and other harmful vapors.

BACKGROUND OF THE INVENTION

Ultra-trace analysis of gas-phase explosives and chemical weapons is critical for many homeland security, law enforcement, customs, and military applications. For example, analytical technologies enable detection of improvised explosive devices, unexploded ordinance, munitions hidden in cargo holds, detection in clandestine laboratories, and monitoring for explosives in public areas. In addition, selective trace analysis is vitally important for post-blast forensic applications. A critical need exists for performing selective trace analysis for the presence of explosives in large-volume air samples. Volatility of most explosives is limited and, therefore, ultra-trace analysis techniques are required. Usually non-selective capture is used for concentrating target organic signatures from large volumes of air. However, this approach has the problem of concentrating matrix interferences along with the analyte of interest. Sophisticated laboratory analysis is usually required due to the complexity of the captured sample. Semi-selective, high-affinity capture is desirable to concentrate trace quantities of analyte while discriminating against the matrix background interferences. Selective capture allows a relatively clean fraction to be captured and, because of the enhanced relative purity, can lead to simplified detection. The streamlined analytical system can be made lightweight and field portable without sacrificing performance. To accomplish this goal, new polymers that provide for reproducible and specific adsorption are needed.

SUMMARY OF THE INVENTION

In one aspect the invention is a method that provides for selective capture of gas-phase explosives and weaponized chemical agents. The method includes: depositing a metal β-diketonate polymer onto a preselected surface so as to construct a structure having a suitable or preselected form that is suitable for sampling (i.e., gas-sampling structure) of airborne vapors or gas-phase agents. In use, the gas-sampling structure containing the metal β-diketonate polymer is introduced to, or placed in, a sampling area (e.g., a cargo hold), a sampling volume (e.g., a vapor chamber), or a sampling location (e.g., an airport). Any explosives or weaponized chemical agents present in the sampling area or location are selectively captured on the metal β-diketonate polymer of the gas-sampling structure (e.g., gas-sampler).

In another aspect, the invention also includes a method, comprising the steps of: forming a gas-sampling structure of a preselected form that includes a metal β-diketonate polymer operatively disposed on a preselected surface that provides a preselected selectivity for the gas-phase explosive or weaponized chemical agent; introducing the gas-sampling structure into a sampling volume; and selectively binding the gas-phase explosive or weaponized chemical agent in the sampling volume on the polymer of the gas-sampling structure based on the preselected selectivity.

The metal β-diketonate polymer includes a bifunctional bridging ligand and a preselected metal ion center. β-diketonate (dionyl) groups in the bifunctional ligand cross-link with a different metal ion center, which provides polymerization and cross-linking in the metal β-diketonate polymer. Polymer selectivity toward a preselected gas-phase Lewis base analyte (e.g., explosives and weaponized chemical agents) is determined by the Lewis acidity of the polymer, which is defined both by the bridging ligand (and its associated R-groups) and the selected metal ion center. For example, electronic inductive effects provided by R-groups of the ligand can tune the acidity of the metal ion center in the polymer. In various embodiments, the metal β-diketonate polymer includes a metal ion center selected from: La(III), Eu(III), Tb(III), Cu(II), Ni(II), Zn(II), and combinations of these metal ion centers. In other embodiments, lanthanide metal ions and transition metal ions can also be used. Preferred metal β-diketonate polymers for selective capture of explosives include, but are not limited to, e.g., Cu(dihed), Ni(dihed); Zn(dihed); La(dihed); Eu(dihed); Tb(dihed); and combinations of these polymers.

Chemical warfare agents can be expected to exhibit strong chemical interactions. Thus, use of weakly acidic cations [e.g., Zn(II), Cu(II), and other weakly acidic metal cations] combined with electron-donating R-groups in the metal β-diketonate polymers can decrease Lewis acidity of the polymer sufficiently to provide these polymers with ability to selectively capture weaponized agents. Electron-donating R-groups include, but are not limited to, e.g., phenyl ($-C_6H_5$); methyl ($-CH_3$); ethyl ($-CH_2CH_3$); n-propyl; isopropyl; n-butyl; isobutyl; sec-butyl; tert-butyl, and other R-groups, including combination of these R-groups. Longer alkyl chain groups may also be suitable. In general, the longer the alkyl chain, the greater the electron density that can be donated, which in the case of chemical weapons is desirable. Thus, no limitations are intended.

Polymer ligands described herein are bifunctional ligands that are based on a p-di(alkyl-1,3-dionyl)benzene structure that includes a benzene core (or other core constituent) and two R-groups including, e.g., $-CH_3$; $-CF_3$; $-C_3F_7$; $-C_6H_5$; and combinations of these R-groups. In a preferred embodiment, the ligand is p-di(4,4,5,5,6,6,6-heptafluoro-1,3-hexanedionyl)benzene, denoted herein as the $H_2$(dihed) ligand. The preferred bifunctional ligand includes the p-di (alkyl-1,3-dionyl)benzene structure with a benzene core and two R-groups comprised of $-C_3F_7$. Other bifunctional ligands include, but are not limited to, e.g., p-di(3-phenyl-1,3-propanedionyl)benzene [$H_2$(ppb) where R=$-C_6H_5$]; p-di (1,3-butanedionyl)benzene [$H_2$(pbb) where R=$-CH_3$]; and p-di(1,1,1-trifluoro-1,3-butanedionyl)benzene [$H_2$(ptb) where R=$-CF_3$]. Other ligands envisioned for use include, e.g., analogues and derivatives of 1,7,7-trimethylbicyclo [2.2.1]heptane that comprise two β-diketonate groups in geometries that cannot complex with the same metal in the polymer. Other aromatic, cyclic, and bicyclic compounds that include β-diketonate groups in positions that do not complex with the same metal cation can also be used. No limitations are intended.

The metal β-diketonate polymer can be deposited onto a preselected surface using a variety of methods. In one method, a metal β-diketonate polymer is deposited to the surface by dip coating the surface. In one embodiment, the preselected surface is a surface of a solid-phase microextraction (SPME) fiber [e.g., a fused silica fiber (quartz)] that contains a non-polar polymer coating, e.g., PDMS. For example, a 30-µm PDMS fiber means the fused silica fiber includes a 30-µm coating of PDMS on the exterior surface. The surface can also be a filter surface, e.g., a filter comprised of deactivated quartz fiber. In various other embodiments, surfaces include inert chromatographic column support surfaces and capillary column interior surfaces. In one embodiment, the preselected surface is an inert sorbent surface that is comprised of any one of a number of diatomaceous earths or other chromatographic supports. These inert supports are typically coated with a non-polar stationary phase (e.g, PDMS) before coating with the metal β-diketonate polymer. In another embodiment, a column surface is coated with a metal β-diketonate polymer. When advantageous, the column surface can be coated with, e.g., PDMS or a hydrophobic deactivation agent prior to coating with the metal β-diketonate polymer. The method further includes the step of determining the gas-phase explosive or weaponized chemical agent captured on the polymer. In one embodiment, the invention is configured for trace level analysis of the gas-phase explosive or weaponized chemical agent, e.g., at the low parts-per-trillion to upper part-per-quadrillion (v/v) detection limit. The polymers can be incorporated into a variety of analytical formats for use. Analytical formats include, but are not limited to, e.g., stationary phases, chromatographic columns (e.g., packed chromatographic columns), capillary columns; multiple capillary arrays; sorbent tubes; sorbents; filters; solid-phase microextraction fibers (e.g., SPME and other fibers). Results described herein can also extend the invention for uses in other analytical formats. For example, in one preferred embodiment, the metal β-diketonate polymer is coated onto a preselected PDMS-coated solid-phase microextraction fiber, as described hereinabove. Captured analytes can then be determined using a variety of analytical tools and instruments.

In another aspect, the invention is also a sensor device for detection of a gas-phase explosive or a weaponized chemical agent. The sensor device includes: a metal β-diketonate polymer disposed to selectively capture a gas-phase explosive or weaponized chemical agent. Sensor formats include, but are not limited to, e.g., Surface Acoustic Wave (SAW) devices, Quartz Crystal Microbalance (QCM) devices, Surface Plasmon Resonance (SPR) devices, and microcantilever devices, and the like, or combinations of these devices. Detection utilized in conjunction with these sensor devices and formats includes, but is not limited to, e.g., optical detection based on alteration of polymer luminescence; electrochemical detection; microcalorimetric detection; evanescent wave-based detection, infrared absorption detection, and the like, or combinations of these detection methods and devices. No limitations are intended. Metal β-diketonate polymers used in sensor devices and associated components can be deposited using coating techniques such as spray-coating and spin-coating. No limitations are intended.

DETAILED DESCRIPTION

Figure 1:
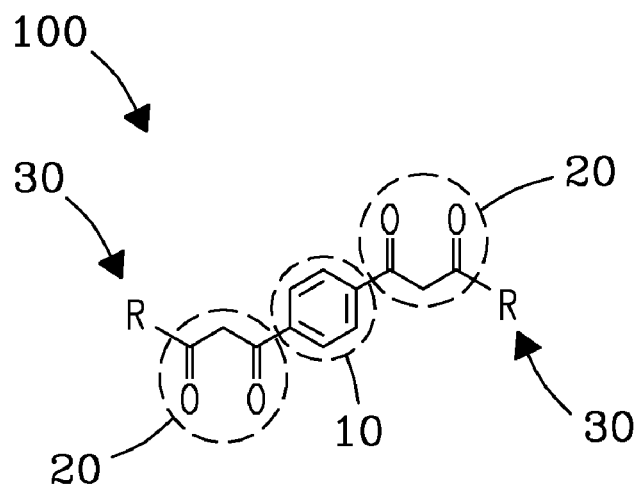
FIG. 1 shows an exemplary ligand of a β-diketonate bridging ligand with selected R-group constituents used in conjunction with the invention, according to various embodiments of the invention.

Described herein is a process that employs metal β-diketonate polymers for selective capture of air-borne analytes including, but not limited to, e.g., explosives and weaponized chemical agents (e.g., nerve agents). Metal β-diketonate polymers are extremely versatile since analyte selectivity and affinity for preselected explosives and/or weaponized chemical agents can be fine-tuned by selection of a suitable metal center and/or a suitable bridging ligand, as described herein. For example, Lewis acidity of the polymer can be preselected based principally on the selection of the metal ion. Lewis acidity of the metal ion can be fine tuned by selection of the appropriate bridging ligand with its electronic inductive effects. Further fine-tuning can be accomplished by exploiting steric properties of the ligand. Ability to tune the affinity makes these polymers useful for selective capture of a broad range of Lewis base target analytes suited to many governmental and industrial applications. For example, metal β-diketonate polymers can be used for large volume air sampling for selective capture of trace quantities of explosives and weaponized chemical agents (also known as chemical weapons, or CW agents) and other harmful vapors for selective trace analysis and determination. These polymers can be incorporated into a variety of useful analytical formats that provide for analysis of trace quantities of explosives and other harmful analyte vapors in a variety of analytical systems. For example, in one embodiment described herein, metal β-diketonate polymers are deposited onto fused silica fibers that contain a PDMS layer (coating) to produce semi-selective, high affinity polymer fibers that selectively capture explosives and weaponized agents in the gas phase at extremely low concentrations for determination and identification of these agents. Analytical formats include, but are not limited to, e.g., solid-phase microextraction (SPME) fibers; capillary column coatings; bundled capillary interfaces (e.g., multicapillary arrays); sorbents, sorbent columns, and sorbent sampling cartridges; and field-portable lightweight automated analysis systems. For example, advantage of using these polymers is their demonstrated semi-selective, high-affinity capture ability. By combining this high affinity and selectivity with sensitive and selective detection, light-weight field-portable instruments with extremely low detection limits can be constructed that operate with a very high reliability. Selective sorbents provide capture of a relatively pure fraction which allows field-portable instrumentation to be constructed or, alternatively, the processing of larger volumes of air before matrix interferences become problematic. Applications further include, but are not limited to, e.g., detection of explosives in cargo holds, detection of unexploded ordinance (UXO), detection of improvised explosive devices (IEDs), detection of explosives and weaponized chemical agents in vehicles, public areas, clandestine laboratories, building ventilation systems, and other large volume air sampling applications. These and other applications in Homeland Security, Law enforcement, Customs, Military, and in the Intelligence Community can be envisioned. Thus, no limitations are intended. The invention is also useful for sampling pre-blast and post-blast explosive vapors for forensic analysis.

FIG. 1 shows a generalized structure of a bifunctional β-diketonate ligand 100 used as a component of a metal β-diketonate polymer used in conjunction with the invention. The polymer is described further herein in reference to FIG. 3. The ligand includes a core molecule or constituent 10 as a center construct of the ligand to which two β-diketonate (dionyl) coordinating groups 20 are attached. One or more R-groups 30 are further attached to respective dionyl groups 20 of the ligand, as detailed herein. In the figure, the exemplary ligand 100 is based on p-di(alkyl-1,3-dionyl)benzene, with benzene shown as the core molecule or constituent 10, but is not limited thereto. For example, core constituents other than benzene may also be utilized. Aromatic nuclei including, e.g., naphthalene derivatives that comprise dionyl groups positioned at the 2,6 positions, and bicyclic structures (e.g., camphor derivatives) can be used. In addition, optically active organic compounds including, e.g., camphor (chemical formula: $C_{10}H_{16}O$) (IUPAC name: 1,7,7-trimethylbicyclo [2.2.1] heptan-2-one) and other optically active compounds can be useful core constituents to provide enantiomeric (optical isomer) selectivity. An exemplary, but non-limiting, ligand is 3,6-di(heptafluorobutanoyl)-1,7,7-trimethylbicyclo [2.2.1] heptan-2,5-dione. This optically active ligand contains bifunctional β-diketonate coordinating groups in a geometry that promotes the desired polymerization. R-groups 30 are preselected to achieve a desired inductive and/or steric effect in the metal β-diketonate polymer. Preferred R-groups 30 for selective capture of explosives include, but are not limited to, e.g., —$CH_3$; —$CF_3$; —$C_3F_7$; —$C_6H_5$ and other R-groups as disclosed herein. In other embodiments that provide selective capture of weaponized chemical agents, additional R-groups may be used including, but not limited to, e.g., ethyl, propyl, butyl, and higher alkyl homologues, with branched analogues being more preferred due to a greater electron donating effect. Incorporation of an optically active R-group, e.g., a sec-butyl or 1,2,2-trimethylpropane functionality, is an alternative to using an optically active core constituent to impart enantiomeric selectivity to the metal β-diketonate polymer. All R-groups as will be selected by those of skill in the art in view of the disclosure are within the scope of the invention. No limitations are intended.

Metal β-diketonate polymers described herein are preferably synthesized using p-di(4,4,5,5,6,6,6-heptafluoro-1,3-hexanedionyl)benzene, denoted herein as the $H_2$(dihed) ligand 100 or (dihed) ligand 100, but is not limited thereto. For example, analogs with different side chains (R-groups) can also be produced, e.g., as detailed by Wenzel et al. [J. Chromatogr. 463 (1989) 171], which reference is incorporated herein. Geometry of each β-diketonate group 20 in the ligand (including the respective R-groups 30), prevents coordination of both β-diketonate groups to the same metal ion. This unique geometry promotes polymerization and cross-linking to other metal centers in the polymer.

Figure 2:
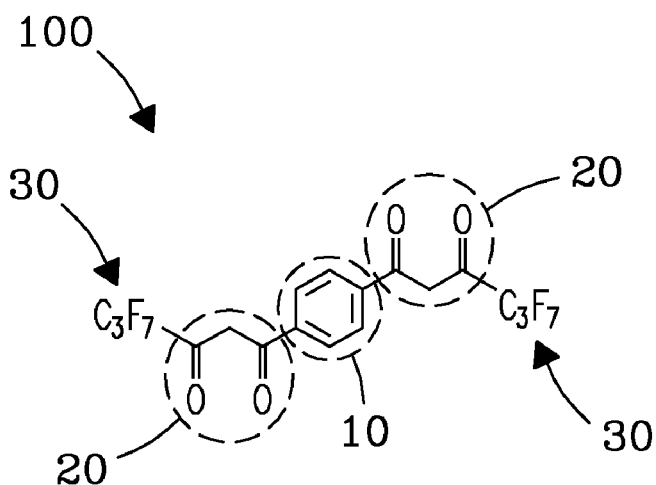
FIG. 2 shows a chemical structure of an exemplary β-diketonate ligand, i.e., H$_2$(dihed), according to a preferred embodiment of the invention.

FIG. 2 shows the structure of a preferred ligand, i.e., $H_2$(dihed) ligand 100. In the figure, the ligand includes a core constituent 10 of benzene. Two (2) dionyl groups 20 are attached to the benzene ring at the para-positions. The ligand further includes one or more terminal R-groups 30 comprised of a —$C_3F_7$ moiety 30 (i.e., —$CF_2CF_2CF_3$) that are attached to respective dionyl groups in the ligand. Electron withdrawing properties of the fluorinated R-groups accentuate the Lewis acidity of the metal ion center ligand (FIG. 3) when the ligand is incorporated in the metal β-diketonate polymer. Synthesis of the $H_2$(dihed) ligand is detailed, e.g., by Picker et al. [J. Chromatogr. 203 (1981) 29], which reference is incorporated herein. The (dihed) ligand is prepared by reaction of 2 moles of ethylheptafluorobutyrate with 1 mole of p-diacetylbenzene in the presence of sodium methoxide. Crude product is purified by repetitive recrystallization. Synthesis of the metal β-diketonate polymer involves addition of the ligand to a solution containing the selected metal cation. A small excess of metal is used and the ligand is added slowly. Product is washed to remove any excess metal ions.

Figure 3:
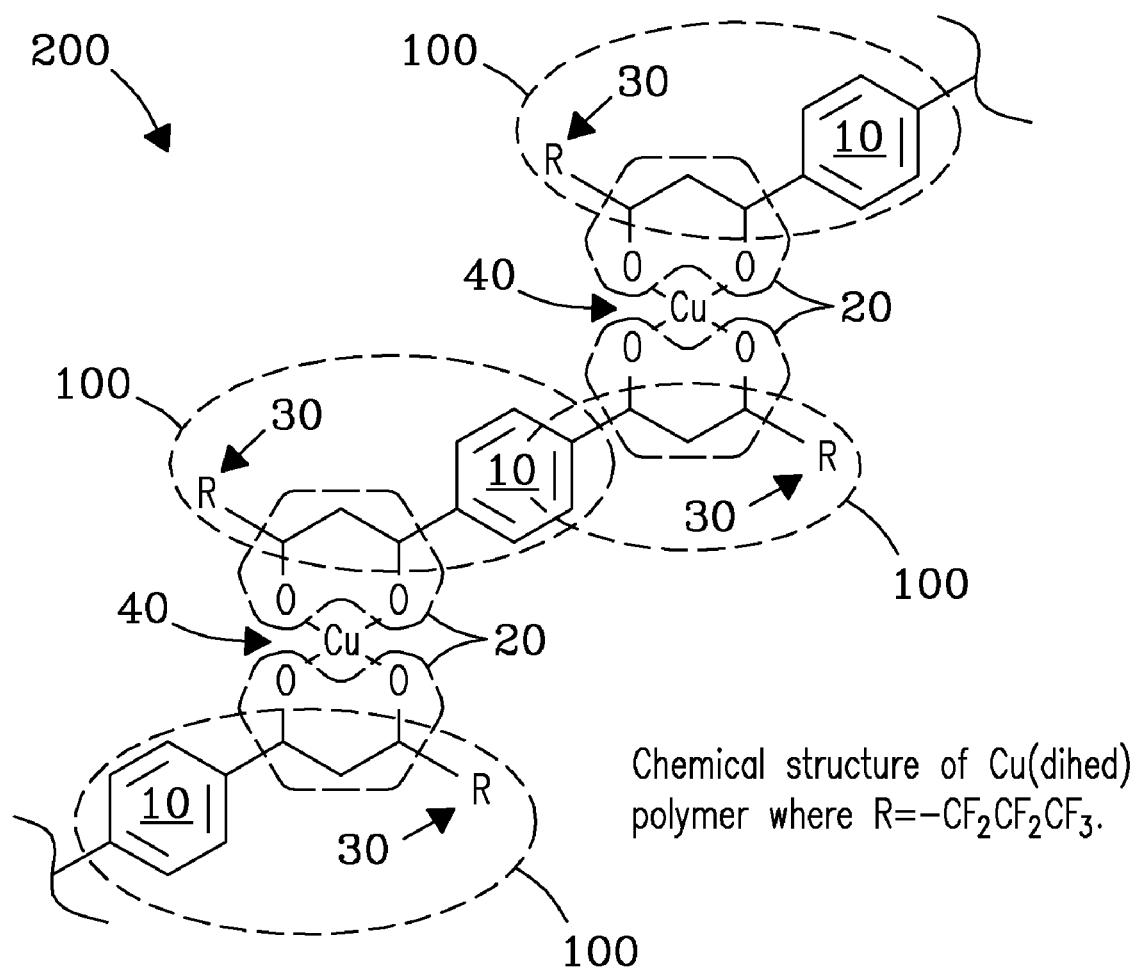
FIG. 3 shows a chemical structure of an exemplary metal β-diketonate polymer, i.e., Cu(dihed), according to another embodiment of the invention.

FIG. 3 illustrates a proposed structure of an exemplary metal β-diketonate polymer 200, i.e., Cu(dihed). The polymer includes a (dihed) ligand 100 with R-groups 30 comprised of —$C_3F_7$ (i.e., —$CF_2CF_2CF_3$). The ligand is coordinated with copper metal ion centers 40 through dionyl groups 20 in the ligand that attach to benzene 10 as a core constituent 10. As indicated previously, this para β-diketonate bifunctionality promotes polymerization (crosslinking), since both β-diketonate groups in each ligand cannot coordinate with the same metal ion center due to geometrical considerations. Metal β-diketonate polymers include, but are not limited to, e.g., La(dihed), and Zn(dihed), described further herein. Preferred metal ion centers 40 in the metal β-diketonate polymers 200 include, but are not limited to, e.g., La(III), Eu(III), Tb(III), Cu(II), Ni(II), and Zn(II). Other lanthanide and transition metal ions can also be used. Elemental analysis of the product ensures atomic composition ratios are consistent with hypothesized polymeric products. The Cu(dihed) polymer is prepared by adding a methanol solution containing the ligand to a cupric acetate solution. The resulting metal β-diketonate polymer (1:1 molar ratio of ligand to polymer) is then collected as a precipitate.

Preparation of the La(dihed) polymer is somewhat more complex. The ligand in the methanol solution is neutralized with aqueous sodium hydroxide to remove acidic β-diketonate hydrogen. The neutralized solution is then slowly added to a solution containing lanthanum nitrate hexahydrate dissolved in methanol. The precipitated product (metal:ligand ratio is 2:3 in this polymer) is collected by filtration, and thoroughly dried in vacuo under phosphorus pentoxide. For some lanthanide polymers, e.g., Eu(dihed), the proposed polymer structure comprises mixed ligand-hydroxo compounds. Here, average molecular weight of the Eu(dihed) polymer is estimated to be 1411 as determined by vapor pressure osmometry [see J. E. Picker and R. E. Sievers, J. Chromatogr., 203:29-40 (1981); T. J. Wenzel, L. W. Yarmaloff, L. Y. St. Cyr, L. J. O'Meara, M. Donatelli; and R. W. Bauer, J. Chromatogr., 396:51-64 (1987)].

Analytes

Figure 4:
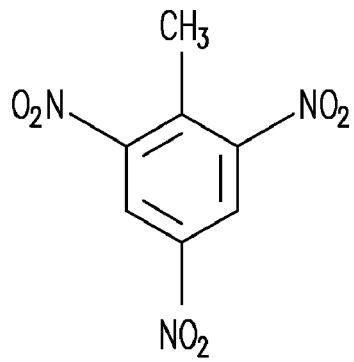
FIG. 4 shows exemplary explosives that are selectively captured by the invention.
Figure 4:
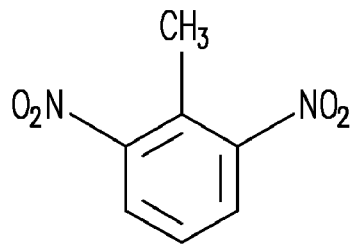
Figure 4:
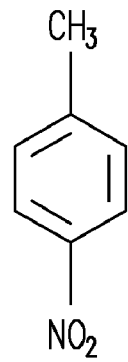
Figure 4:
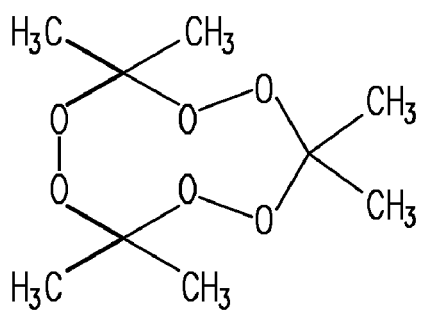
Figure 4:
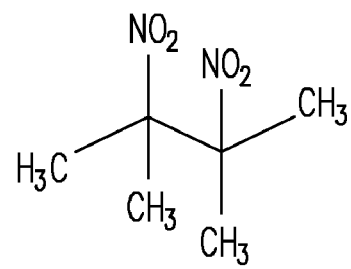
Figure 4:
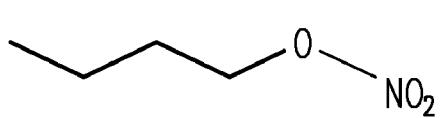
Figure 4:
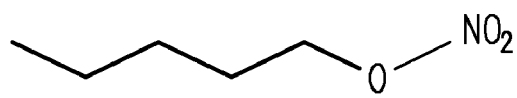

Analytes of a national security interest include, but are not limited to, e.g., explosives, CW agents, and organic nuclear signature compounds including, e.g., tributyl phosphate. Many of these analytes have a characteristic basicity or otherwise basic character, which can be exploited to provide selective retention by the metal β-diketonate polymers. FIG. 4 shows representative chemical structures for explosives, explosive components, and related compounds captured by the invention. Explosive classes include, but are not limited to, e.g., nitroaromatics; nitrate esters; nitroalkanes; and peroxide-based explosives. Exemplary nitroaromatic explosives include, but are not limited to, e.g., 2,4,6-trinitrotoluene (TNT); 2,6-dinitrotoluene (2,6-DNT); and 4-nitrotoluene (4-NT). Exemplary nitroalkanes include nitroalkane taggants, including, but not limited to, e.g., 2,3-dimethyl-2,3-dinitrobutane (DMDNB). The term "taggant" as used herein means a chemical or physical marker that is added to an explosive as a means to trace the source, origin, or manufacturer of the explosive. DMDNB is a typical volatile compound added to explosive formulations to aid in detection. Peroxides include, but are not limited to, e.g., triacetone triperoxide (TATP). Exemplary nitrate esters include: n-butyl nitrate (BN); and n-pentyl nitrate (PN). These esters were chosen as stable analogs of explosives such as nitroglycerine (NG), ethylene glycol dinitrate (EGDN), and pentaerythritol tetranitrate (PETN). Capture of aromatic nitro explosives such as TNT and tetryl are based on the electron rich nature of the nitro group. While nitro aromatics are often considered electron deficient, only the aromatic ring is electron deficient. Individual nitro groups are basic and thus electron rich, which provides for their selective retention on the metal β-diketonate polymers. In addition, these polymers will also capture nitrate esters (NG, EDGN, and PETN), nitramines (RDX and HMX), and peroxide (TATP) explosives. Various explosive classes have different basic characteristics and, therefore, can be expected to display predictable retention on the metal β-diketonate polymers.

Tailoring of Polymers for Selective Capture of Analytes

Metal β-diketonate polymers can be constructed to achieve selective capture of various analytes of interest. For example, Lewis acidity of these polymers can be easy tailored during synthesis for a desired application. Polymer selectivity is dictated principally by three parameters. A first parameter is the choice of metal ion. Each metal ion also has a characteristic Lewis acidity that can be predicted by the ionic radius and charge. A trivalent cation such as La(III), e.g., will be more acidic than a divalent cation such as Zn(II) or Cu(II). Affinity for an analyte of interest can therefore be defined by selection of the metal cation. For example, β-diketonate polymers that incorporate La(III) exhibit a stronger interaction compared to Cu(II) due to the +3 charge of the La(III) ion. A second parameter that determines acidity of the Lewis acid is the electronic inductive effects of the selected ligand. Exemplary R-groups include, but are not limited to, e.g., —$C_6H_5$ [resulting ligand: $H_2$(ppb)]; —$CH_3$ [resulting ligand: $H_2$(pbb)]; —$CF_3$ [resulting ligand: $H_2$(ptb)]; and —$C_3F_7$ [resulting ligand: $H_2$(dihed)]. These side chains have electronic inductive effects that modulate the Lewis acidity of the metal center. Fluorinated ligands, for example, withdraw electron density from the coordination sphere which accentuates the Lewis acidity of the metal center. Other ligands with selected R groups (e.g., phenyl or alkyl groups) can donate electron density and thus decrease overall Lewis acidity. A third parameter that determines selectivity is the steric effects of a selected ligand. For example, interaction strength between the metal β-diketonate polymer and the analyte of interest can be modified using steric effects to tune the selectivity. For example, a ligand containing bulky substituents can hinder access to the metal coordination sphere by a Lewis base analyte. Here, the analyte must first penetrate the steric shield afforded by the ligand before it can donate electron density to the metal coordination sphere. In such a case, the polymer/analyte interaction is attenuated. In sum, parameters described herein are easily adjusted during synthesis to give a metal β-diketonate polymer with a preselected interaction strength for a given or desired application. Other selected parameters may improve capture kinetics, polymer stability, and analyte selectivity. Thus, no limitations are intended.

Capacity Factor

Capacity factor (k') is a measure of the retention ability of a chromatographic column for an analyte of interest. The capacity factor is given by equation [1] as the ratio of the difference between the analyte retention time ($t_R$) and the column dead time ($t_O$) divided by the dead time ($t_O$), as follows:

$$k' = \left(\frac{t_R - t_O}{t_O}\right) \qquad [1]$$

The reduced retention time ($t_R - t_O$) is the time required to elute an analyte minus the time required for a non-retained compound to traverse the column. Methane is often used in gas chromatographic studies to determine the dead time for a selected column. Dead time is a geometrical parameter that is independent of the types of analytes and the mobile phase.

A control column (8 ft.×⅛ in. O.D.) was packed with a diatomaceous earth, e.g., CHROMOSORB-W HP® (a registered trademark of Celite Corporation, Santa Barbara, Calif., USA) available commercially (Supelco, Bellefonte, Pa., USA) as an inert support material, which was coated with 3% PDMS (w/w). Experimental columns were prepared using the same support material additionally coated with a 5% (w/w) loading of selected metal β-diketonate polymers. TABLE 1 lists capacity factors for selected explosives at selected temperatures.

TABLE 1

Capacity factors and capacity factor ratios for the analysis of explosives and related compounds on metal β-diketonate polymers.

| Capacity Factor Ratio/Compound (at ° C.) | $K'_{control}$ | $k'_{Zn(dihed)}/k'_{control}$ | $k'_{Cu(dihed)}/k'_{control}$ | $k'_{La(dihed)}/k'_{control}$ |
|---|---|---|---|---|
| TNT (190° C.) | 1.89 | 1.74 | 2.45 | 12.54 |
| 2,6-DNT (170° C.) | 1.45 | 1.87 | 2.82 | 21.93 |
| 4-NT (165° C.) | 0.71 | 2.28 | 4.91 | 36.62 |
| BN (75° C.) | 1.18 | 4.05 | 7.74 | a |
| PN (75° C.) | 2.46 | 5.05 | 8.38 | a |
| DMDNB (110° C.) | 3.05 | 4.58 | a | a |
| TATP (90° C.)[b] | 4.96 | 2.18 | a | a |

[a]Compound either decomposed or was too strongly retained to elute.
[b]Elution of intact analyte could be verified by MS.

Compounds shown in TABLE 1 represent a broad range of volatile explosive compounds including representatives from the nitro aromatic (TNT, 2,6-DNT, and 4-NT), nitrate ester (BN and PN), peroxide-based (TATP), and the taggant (DM-DNB) classes. In general, interactions between the metal β-diketonate polymers and explosives increased in the following order: Control<Zn(dihed)<Cu(dihed)<<La(dihed). Interaction strengths for the [La(dihed)] ligand, i.e., La(III) complex of p-di(4,4,5,5,6,6,6-heptafluoro-1,3-hexanedionyl)benzene, shows 13-42 times greater retention for nitro aromatic compounds compared to a control column (identical column but lacking the 5% loading of the metal β-diketonate polymer). Nitrate esters, the peroxide explosive triacetone triperoxide, and the taggant 2,3-dimethyl-2,3-dinitrobutane were too strongly retained to elute from the La(dihed) column. These compounds were observed to elute using a less retentive Cu(dihed) or Zn(dihed) column.

In general, capacity factor studies demonstrated a robust retention of target explosives on columns containing metal (dihed) polymers compared to control columns. Capacity factor experiments described hereinabove also demonstrated that metal β-diketonate polymers exhibit a strong affinity toward explosives. However, before a candidate metal β-diketonate polymer is deemed suitable for use, its selectivity relative to matrix interferences should be demonstrated. For example, certain materials, like carbon-based sorbents, while expected to show strong affinity in general toward organic compounds including explosives, the selectivity relative to background organic matrix components is not expected to be high. Thus, overall properties are not advantageous for selective capture.

Experiments described hereafter investigated the selectivity of the metal β-diketonate polymers relative to matrix background compounds using a chromatographic measurement termed the Kováts index.

Kováts Retention Index

The Kováts (retention) index (I) quantifies relative elution times and retention times of compounds on different stationary phases. The Kováts index is experimentally determined by bracketing an analyte of interest between retention times for two n-alkanes that differ in size by one methylene unit, i.e., a shorter (smaller) alkane and longer (larger) alkane. The Kováts index is independent of many chromatographic variables including, e.g., column dimensions, column format (packed or capillary), and carrier gas flow rate. The isothermal Kováts index (I) is given by equation [2], and involves a linear relationship between values of [log(t$_r$')] and the number of carbon atoms in the organic compound or molecule, as follows:

$$I = 100 \times \left[ n + (N - n) \frac{\log(t'_{r(unknown)}) - \log(t'_{r(n)})}{\log(t'_{r(N)}) - \log(t'_{r(n)})} \right] \quad [2]$$

Here, (n) is the number of carbon atoms in the smaller n-alkane; (N) is the number of carbon atoms in the larger n-alkane; and (t$_r$') is the adjusted retention time. The Kováts index is ideally suited to define selectivity since the index determines retention relative to non-polar hydrocarbons (n-alkanes). Hydrocarbons are major matrix interferences encountered in large-volume air samples. In exemplary tests, the Kováts index was used to assess the retention selectivity of various metal β-diketonate polymers, i.e., (dihed) polymers, for an exemplary gas-phase explosive, i.e., TNT. Experiments were conducted at the same temperature to allow direct comparison of Kováts index values. Results are presented in TABLE 2.

TABLE 2

Kováts index values for exemplary metal (dihed) columns.

| COLUMN | TEMPERATURE (° C.) | KOVÁTS INDEX (TNT) |
|---|---|---|
| Control | 200 | 1662 |
| Cu(dihed) | 200 | 1784 |
| La(dihed) | 200 | 2124 |

Kováts values of 1600 and 1700 correspond to a retention time for n-$C_{16}$ and n-$C_{17}$ n-alkanes, respectively. A Kováts increment of 100 corresponds to a retention time for a methylene unit ($CH_2$). A Kováts value of 1662 thus indicates that TNT elutes at a time between an n-$C_{16}$ and an n-$C_{17}$ alkane. From TABLE 2, the La(dihed) column exhibits a selectivity for TNT that is 4.62 methylene units greater than that of the control [i.e., (2124 minus 1662)/100=4.62]. This result demonstrates that La(dihed) exhibits a very high selectivity for TNT relative to nonpolar hydrocarbons. In general, these metal β-diketonate polymers displayed ideal characteristics of both high affinity (as indicated by the capacity factors) and high selectivity (as indicated by Kováts index values) toward explosives. Kováts index results are particularly relevant since hydrocarbon components are known to be principle matrix interferences in air samples.

Analysis of Explosives

Figure 5:
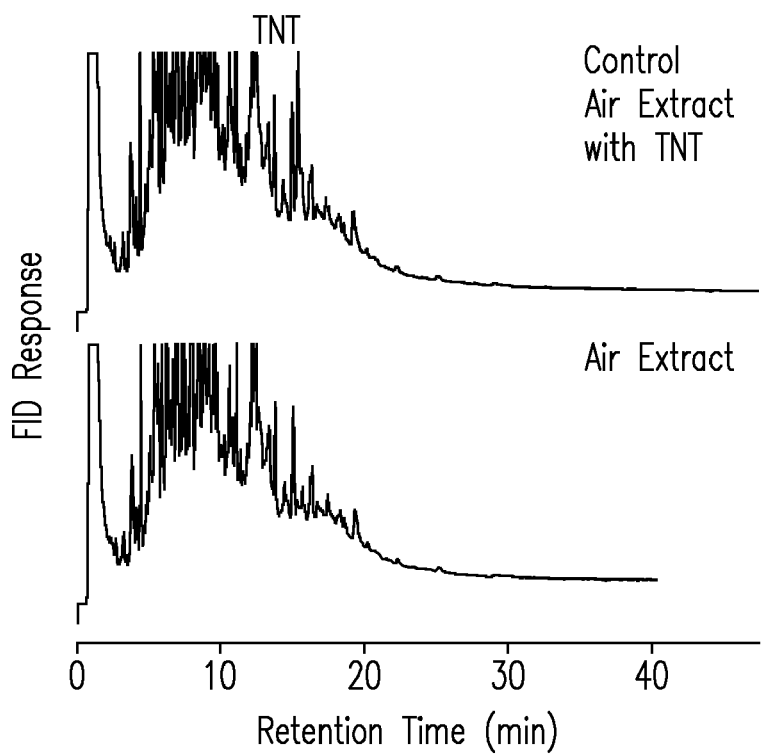
FIG. 5 compares chromatograms for a TNT-spiked air extract concentrate (top) to a non-spiked air extract concentrate (bottom) on a column packed with a control support material.
Figure 6:
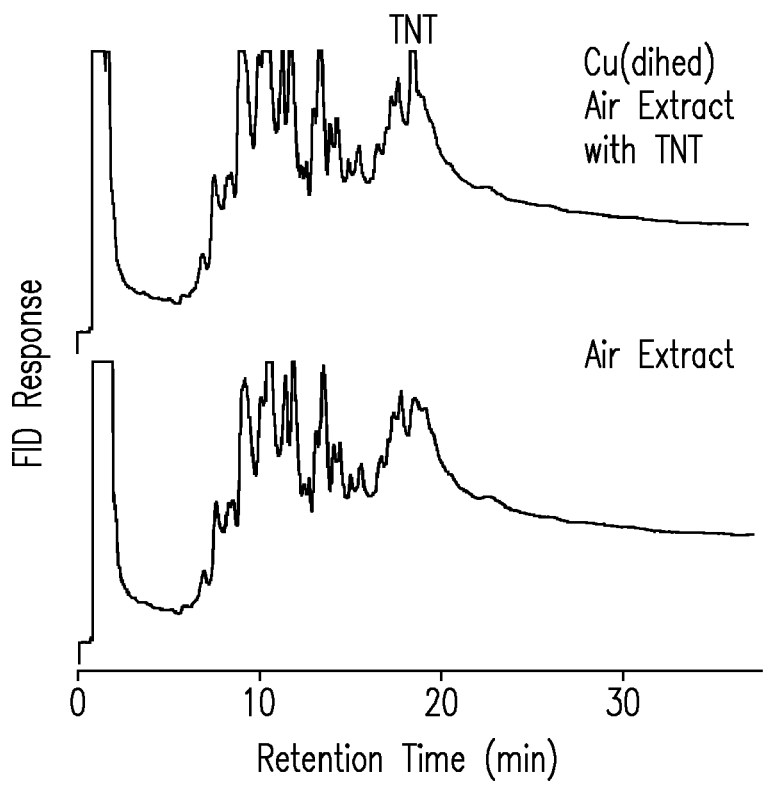
FIG. 6 compares chromatograms for a TNT-spiked air extract concentrate (top) and a non-spiked air extract concentrate (bottom) eluted on a chromatographic column comprised of the control support material that further included an additional loading of an exemplary Cu(dihed) metal β-diketonate polymer.
Figure 7:
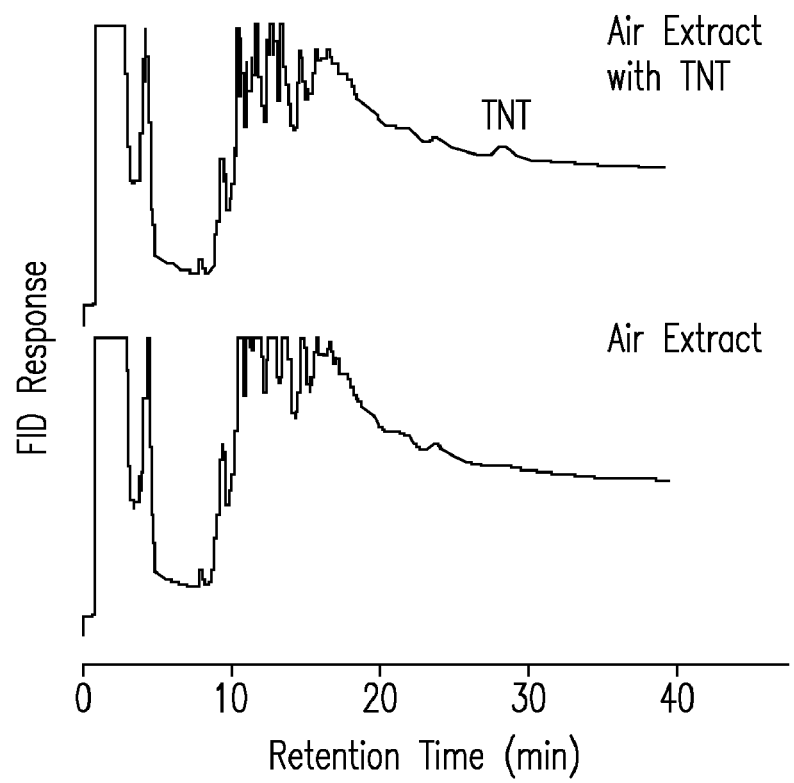
FIG. 7 compares chromatograms for a TNT-spiked air extract concentrate (top) and a non-spiked air extract concentrate (bottom) eluted on a chromatographic column comprised of the control support material that further included an additional loading of an exemplary La(dihed) metal β-diketonate polymer.
Figure 8:
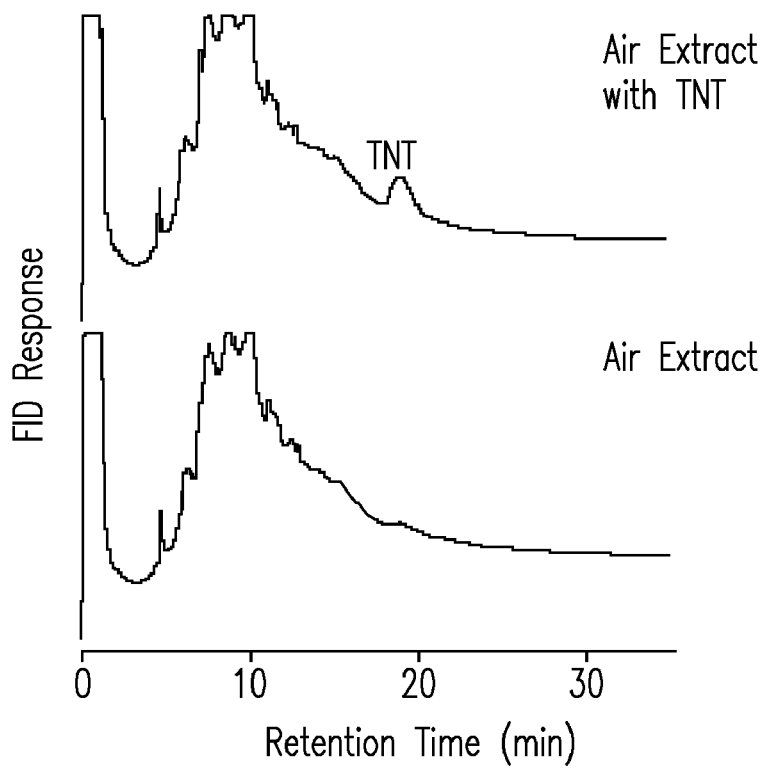
FIG. 8 compares chromatograms for a TNT-spiked air extract concentrate (top) and a non-spiked air extract concentrate (bottom) eluted on a chromatographic column with a decreased column length comprised of the control support material that further included an additional loading of an exemplary La(dihed) metal β-diketonate polymer.

Proof-of-principle experiments were performed using temperature programmed runs to measure ability of metal β-diketonate polymers to selectively retain TNT relative to the matrix interferences. Separations shown in FIGS. 5, 6, and 7 below used a temperature program that started at 50° C. for 2 minutes followed by a 10° C./minute ramp to a final temperature of 200° C. Control columns (8 ft.×⅛ in. O.D.) were packed with CHROMOSORB W HP® (Sigma-Aldrich, St. Louis, Mo., USA), a diatomaceous earth, used as an inert support material, that included a 3% (w/w) loading of PDMS. Experimental columns were prepared using the same support material as the controls which additionally included a 5% loading (w/w) of a selected metal β-diketonate polymer. TNT-spiked air extract concentrate samples and non-spiked air samples were compared using a column containing selected metal β-diketonate polymers against a control column (identical column but lacking a 5% loading of the selected metal β-diketonate polymer). TNT was spiked to correspond to an extrapolated air concentration level of 47-ppt (v/v). In one embodiment, the column included Cu(dihed) polymer. FIG. 5 compares chromatograms for a TNT-spiked air extract concentrate (top) and a non-spiked air extract concentrate (bottom) eluted on control columns (no metal β-diketonate polymers). In the figure, TNT has a standard retention time of 15.30 min (control). The explosive elutes in an area of considerable matrix interference, which is reflected in the recovery value of 138% calculated from the integrated peak area referenced to a 100% standard. The recovery is high due to co-elution of interferences. FIG. 6 shows the separation achieved under temperature programmed conditions on a column loaded with Cu(dihed), which resulted in a retention time for TNT of 18.74 min. The Cu(dihed) column has intermediate retention for explosives (see TABLE 1). As shown, the explosive eluted in the midst of numerous matrix components. The calculated recovery of 157% reflects the presence of severe co-eluting interferences. Inspection of the chromatograms indicated that phases with yet higher selectivity for TNT would be advantageous for this application. Based on these Cu(dihed) range-finding experiments, the TNT separation was repeated on a La(dihed) column. FIG. 7 compares chromatograms for a TNT-spiked air extract concentrate (top) and a non-spiked air extract concentrate (bottom) eluted on a column containing a 5% (w/w) loading of La(dihed) polymer, another exemplary metal β-diketonate polymer. In the top chromatogram, the injection corresponds to 200 L of air that contains an extrapolated 47 ppt (v/v) of TNT. Chromatograms show TNT elutes with a retention time of 30.01 min. In addition, TNT is retained well beyond any matrix interferences. The near quantitative recovery of 110%, as well as inspection of the TNT retention window in the non-spiked sample (bottom chromatogram), indicate a complete lack of matrix interferences. Use of the La(dihed) polymer clearly provides adequate selectivity for successful analysis of TNT in air samples. However, considerable column bleed was observed at the upper temperature of 200° C. Column bleed observed in the figure is due to limited thermal decomposition of the stationary phase at elevated temperatures. These decomposition products can "bleed" from the column causing an elevated baseline. In general, use of metal β-diketonate polymers as stationary phases in columns is preferably limited to a temperature maximum of about 180° C. Since the stationary phase contains a heavily fluorinated ligand, decomposition products can be expected to cause severe interferences with certain detection modes sensitive toward halogenated species (e.g., electron capture detection, negative chemical ionization mass spectrometry, or ion mobility spectrometry). The column bleed can be reduced, however, using strategies known by those of skilled in the chromatographic and chemical arts including, but not limited to, e.g., chemical cross-linking, covalent incorporation of the metal β-diketonate polymer into, e.g., the poly (dimethylsiloxane) (PDMS) stationary phase, or simple approaches such as shortening the column length. The latter approach is effective since there is less stationary phase to contribute to column bleed and, in addition, lower temperatures can be used to accomplish analyte elution. As noted herein, selective retention value of TNT is larger than required to separate the explosive from the matrix components. Therefore, the La(dihed) column can be shortened as a strategy for reducing column bleed. Preliminary tests demonstrated that a reasonably sharp TNT peak and a significant decrease in column bleed was observed using a temperature ramp that stopped at a maximum temperature of 180° C. rather than 200° C., but is not limited thereto. All temperature ramping processes and temperature profiles as will be selected by those of skill in the chromatographic arts in view of the disclosure are within the scope of the invention. FIG. 8 compares chromatograms for a TNT-spiked air extract concentrate (top) and a non-spiked air extract concentrate (bottom) that were eluted on a chromatographic column containing La(dihed) polymer that had a decreased column length (2 ft.×⅛ in. O.D.), eluted using a modified temperature program. In the figure, selective retention of TNT (retention time of 19.15 min) is still adequate to pull this compound away from the majority of matrix interferences. This is reflected by the calculated recovery of 113%. Shortening the column from 8 ft. to 2 ft. had the desirable effect of dramatically decreasing the column bleed. With the decreased column bleed implementation of more selective and sensitive detection can now be initiated. The studies described hereinabove used metal (dihed) polymers coated on inert supports which were then packed into gas chromatographic columns. Although effective for the separation of TNT in an air extract concentrate, the packed column format is not appropriate for some compounds due to excessively strong interactions. For example, packed column GC using La(dihed) was not successful for analyzing nitrate esters, DMDNB, or TATP. Similarly, interactions on Cu(dihed) were too strong for analysis of TATP and DMDNB. Zn(dihed) was one phase that allowed analysis of all the target compounds. Other formats may also offer attenuated interaction strengths and, therefore, allow analysis of target analytes that are too strongly retained on packed columns. Thus, no limitations are intended.

Analytical Formats

Proof-of-principle experiments are described that employ metal β-diketonate polymers in exemplary analytical formats including, but not limited to, e.g., stationary phases, chromatographic columns (e.g., packed chromatographic columns), sorbents packed in tubes, solid-phase microextraction coatings, and a variety of sensor formats. Metal β-diketonate polymers can also be used in other analytical formats. Thus, no limitations are intended. All analytical formats implemented by those of skill in the art in view of the disclosure are within the scope of the invention. For example, many uses of fibers coated with metal β-diketonate polymers, can be envisioned. In one embodiment, for example, field-portable analytical instruments interfaced with automated compact GC instruments can be envisioned that incorporate selective solid-phase micro-extraction (SPME) fibers coated with metal β-diketonate polymers for monitoring or sampling of air space environments for the presence of explosives and chemical weapons. Ultra-trace analysis of explosives in air requiring selective chromatographic preconcentration coupled with sensitive and selective detection can also be performed. In addition, single stand-alone sensors that employ metal β-diketonate polymer coated fibers for capture of selected gas-phase analytes are also within the scope of the invention. SPME fibers and capillary columns coated with selected metal β-diketonate polymers described herein may also offer lower retention to allow for analysis of strongly retained analytes that cannot be currently addressed by packed column GC. Field-portable analytical systems and other promising analytical formats based on use of these polymers can also be expected. For example, the invention is compatible for uses in sensor development based on a number of transduction principles including, but not limited to, e.g., changes in luminescence that occur upon interaction of certain luminescent metal β-diketonate polymers (e.g., most notably those containing Eu(III), Tb(III)) with Lewis base analytes such as explosives. All analytical formats that will be implemented in view of this disclosure by those of ordinary skill in the art are within the scope of the invention. No limitations are intended.

SPME Fibers Coated with Metal β-Diketonate Polymers

Proof-of-principle experiments were conducted that focused on analytical sampling using the solid-phase microextraction (SPME) format. As used herein, the term "SPME" refers to a solid-phase microextraction composition or process that involves use of fused silica fibers coated with non-polar polymers, e.g., polydimethylsiloxane (PDMS) or other solid-phase microextraction fibers. In various embodiments, SPME fibers are coated with at least one selected β-diketonate polymer and used for sampling of a gas-phase explosive. Solid-phase microextraction (SPME) fibers can be coated by dipping the fiber into a concentrated solution that contains the dissolved metal β-diketonate polymer. Coated fibers may be placed in, or within, a selected location (e.g., an airport location) for capture, and selective retention of, gas-phase analytes. The prepared fibers thus provide for sampling of preselected gas-phase or airborne explosives within that location. Locations are not limited.

In an exemplary test, PDMS fibers were coated with a La(dihed) polymer. Here the fibers were prepared by dip coating the La(dihed) polymer onto a PDMS fiber, which formed a fairly uniform La(dihed) layer on top of the non-polar PDMS. After thermal conditioning for 30 min. at 180° C. under helium flow, the fibers were ready for use. Initial tests exposed fibers overnight to saturated TNT air samples using a saturation tank (a flake of military-grade TNT in a capped vial). After sampling, coated fibers were analyzed by GC/MS. Results are presented in TABLE 3.

TABLE 3

Quantity of TNT captured on the La(dihed) experimental and control fibers exposed overnight to a saturated TNT vapor.

| FIBER | TNT (nanograms on fiber) |
| --- | --- |
| 7-μm La(dihed) | 12.33 |
| 7-μm (control) | 3.61 |
| 7-μm La(dihed) | 8.21 |
| 7-μm (control) | 2.42 |
| 30 μm La(dihed) | 16.06 |
| 30-μm (control) | 7.38 |
| 30 μm La(dihed) | 12.22 |
| 30-μm (control) | 6.04 |

Results show a prominent enhancement in the quantity of captured TNT on the metal β-diketonate-coated SPME fiber compared to PDMS controls. In particular, results show the La(dihed)-coated fibers have a far greater affinity for TNT relative to the PDMS controls. La(dihed) fibers also captured a greater quantity of 2,4-DNT (a TNT impurity), than did the control (data not shown). 30-μm fibers coated with La(dihed) picked up more TNT on an absolute basis than the 7-μm coated fibers; however, relative to the PDMS controls, the 7-μm fibers displayed better performance than the 30-μm fibers. The superior relative performance of the 7-μm fibers was attributed these fibers being easier to coat, a property that resulted in a larger La(dihed) phase volume compared to the 30-μm fibers (as determined by scanning electron microscopy).

Coated fibers were also placed, and tested, in an explosives bunker prepared from a cargo container ("seatainer") that contained a steel ammunition magazine. Air was sampled in both the magazine and in the bunker room. Fibers were allowed to sample the air for 48 to 72 hrs. Early GC/MS experiments identified TNT and 2,4-DNT (by retention times and mass spectra) on fibers used to sample air in the magazine. Since the bunker contained small amounts of 2,4-DNT in addition to bulk TNT, it is unknown whether the 2,4-DNT originated from the neat 2,4-DNT sample or was seen because it is an impurity in the bulk TNT. To increase sensitivity for 2,4-DNT and TNT in subsequent analysis runs, fibers were analyzed under Selected Ion Monitoring (SIMS) conditions. A detection limit of about 1 picogram (pg) (S/N=3) for each analyte was achieved using this approach. Results are summarized in TABLE 4.

TABLE 4

Quantity of TNT captured on the La(dihed) experimental and the PDMS control fibers when exposed 48 to 72 hrs to air in an explosives bunker.

| SAMPLING LOCATION | FIBER | 2,4-DNT (picograms on fiber) | TNT (picograms on fiber) |
| --- | --- | --- | --- |
| Magazine | 7-μm La(dihed) | 849.4 | 231.4 |
| Magazine | 7-μm (control) | 42.2 | 13.7 |
| Magazine | 30 μm La(dihed) | 848.5 | 65.5 |
| Magazine | 30 μm (control) | 100.3 | 22.3 |
| Seatainer (room air) | 7-μm La(dihed) | 14.5 | 6.9 |
| Seatainer (room air) | 7-μm (control) | 1.70 | <1.0* |
| Seatainer (room air) | 30 μm La(dihed) | 10.7 | 2.4 |
| Seatainer (room air) | 30 μm (control) | 2.5 | ≦1.0** |

*Below Detection Limit
**Analyte is about at the detection limit

Figure 9:
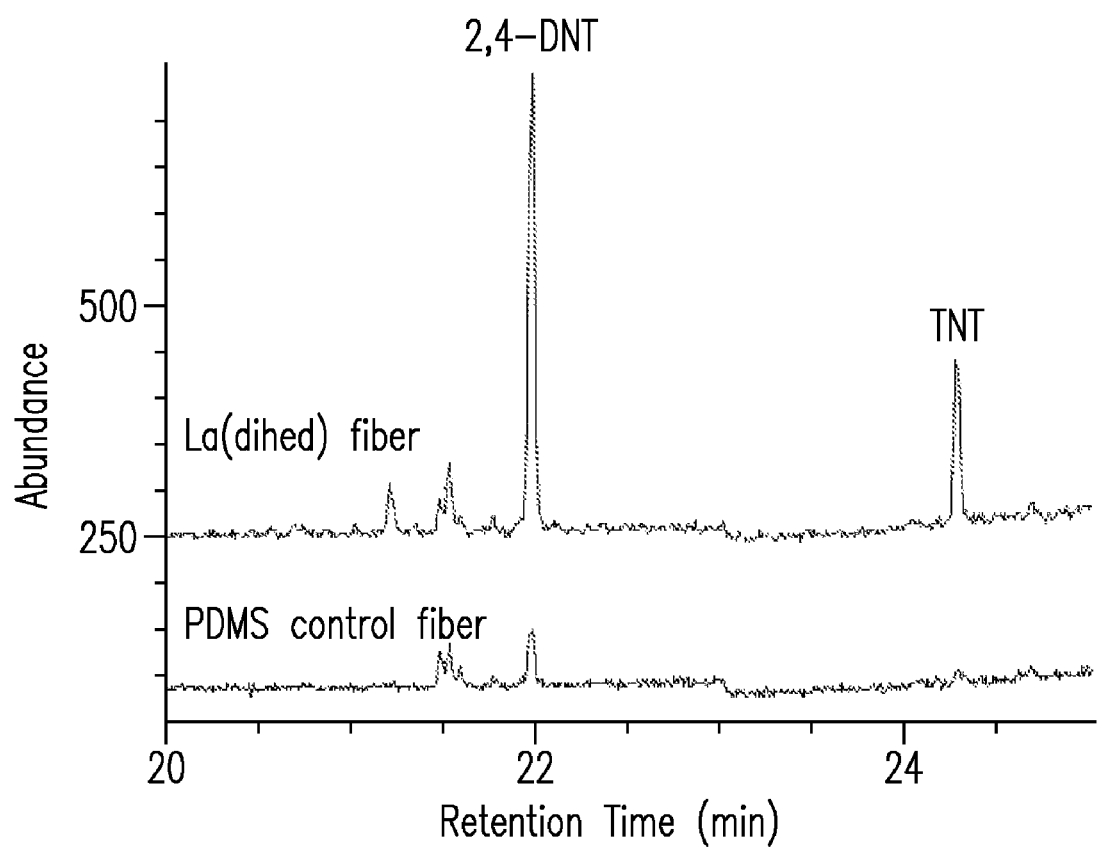
FIG. 9 presents GC/MS selected ion current chromatograms for selected explosives eluted from a La(dihed) coated SPME fiber (top) compared to a PDMS coated control fiber.

FIG. 9 presents chromatograms that compare analyses of bunker room air on a La(dihed) coated fiber (top) to a 7-μm PDMS control fiber (bottom). Analysis proceeds by thermal desorption of the SPME fiber, separation of the components by capillary GC, and detection by SIMS. Results show the advantage of analyzing TNT and 2,4-DNT in the cargo container environment using the high affinity semi-selective La(dihed) polymer compared to non-selective PDMS controls. La(dihed) offers selective capture with much higher affinity for the targets (2,4-DNT and TNT) than non-selective PDMS controls. Detection limit in this analysis was approximately 1 picogram of explosive (S/N=3). Results show that 7-μm La(dihed) fibers captured 20 times the amount of 2,4-DNT and 17 times the quantity of TNT compared to the PDMS control when sampling air within the magazine. In room air, concentration of TNT was estimated to be far less than 3 ppt (v/v). The 7-μm La(dihed) fiber captured 9 times the amount of 2,4-DNT relative to the PDMS control fiber. TNT is well below the detection limit in the bunker room air for analysis using the PDMS control; TNT is not visible in the chromatographic trace. In contrast to the PDMS control, sampling under identical conditions with La(dihed) fibers resulted in a strong signal for TNT. These results are highly significant, since conventional PDMS fibers are often used for ultra-trace analysis. Furthermore, the sampling scenario determines TNT at concentrations and conditions required for analysis of cargo holds for hidden explosives. Therefore, results are highly relevant. The La(dihed) fibers can also be used for multiple runs. Several fibers were used for more than 12 sampling/analysis cycles with no observed degradation in performance. Fibers can be refurbished simply by rinsing the spent (used) fibers in methanol to remove the old La(dihed) coating and applying a fresh La(dihed) coating, e.g., by dipping again in a concentrated methanol solution containing the La(dihed), and drying, e.g., by evaporating solvent in an 80° C. oven for 4 min, and thermally conditioning the coated fibers at 180° C. for 30 min under helium flow. No limitations are intended.

While exemplary embodiments of the invention on SPME fibers have been described, the invention is not limited thereto. For example, another suitable format is to apply a solution (or suspension) of polymer to a deactivated quartz fiber filter and collect analytes (e.g., explosives) directly on the impregnated filter. Analytes on the filter coupon can then be thermally desorbed into a sensitive and selective detector (e.g., ion mobility spectrometer) for detection of the desorbed compounds. Capture on the coated fibers can be selective to a single analyte (e.g., TNT) or a single class of analyte (e.g., nitrate esters), or can be semi-selective to capture more than one analyte or class of analyte (TNT and nitrate esters).

Molecular imprinting can also be used to prepare metal β-diketonate polymers for uses and applications of the invention, e.g., as molecularly imprinted polymers (MIPs). In this approach, the metal β-diketonate polymer is polymerized in the presence of a chemical template that provides proper spatial and/or geometric orientation for selective capture of the desired analyte (e.g., an explosive, or CW agent); a stable or non-toxic surrogate; a structurally similar analogue; or a structurally related compound. Following polymerization, the oriented template is removed, resulting in a polymer with specific cavities that contain three-dimensional binding sites that provide the desired selectivity and affinity for the analyte of interest. However, molecularly imprinted polymers specific toward explosives are difficult to synthesize using traditional free radical polymerization techniques known in the art because nitro groups in the explosives used as the chemical templates scavenge free radicals and interfere with efficient polymerization. In addition, conventional imprinting employs reactive intermediates and elevated temperatures that can degrade sensitive template molecules during the imprinting process. However, making MIPs according to the metal beta-diketonate approach is not expected to suffer from traditional templating problems because polymerization (cross-linking) does not depend on free radical propagation reactions that can be disrupted by the presence of an explosive. Rather, cross-linking is determined by metal coordination in the metal β-diketonate polymers, a process that is not expected to be influenced by the presence of template explosive. In addition, imprinting using the metal β-diketonate polymerization approach is advantageous since the polymerization conditions are very mild, which promotes stability of the template. Thus, this technique can produce explosive-specific, and other agent-specific MIPs.

Other suitable analytical formats include selective capture on sorbents that contain metal β-diketonate polymers; selective capture in bundled capillaries (e.g., ~1000×40 µm I.D. capillaries bundled together that provide a honeycomb cross section having the appearance of a small capillary column with, e.g., a 3 mm O.D. as described hereinabove); optical detection of explosives based on changes in luminescent properties; and selective capture in capillary columns coated with metal β-diketonate polymers. In one application, a static coating in a deactivated fused silica column is envisioned, e.g., using a solution of La(dihed) and PDMS. All analytical formats employed by those of skill in the art in view of the disclosure are within the scope of the invention. No limitations are intended.

Example 1

Preparation of Metal β-Diketonate Polymers

Reagents used for $H_2$(dihed) synthesis included 1,4-diacetyl benzene, ethyl heptafluorobutyrate, sodium methoxide, and diethyl ether. Metal nitrates used for synthesis of metal (dihed) polymers were obtained commercially (Sigma-Aldrich, St. Louis, Mo., USA). Ethanol used for $H_2$(dihed) recrystallization was purchased (Gold Shield Chemical Co., Hayward, Calif., USA).

Example 2

Preparation of Coated SPME Fibers

Two groups of SPME fibers were examined, a group that was coated with 7-µm poly(dimethylsiloxane) (PDMS) and one coated with 30-µm PDMS. One fiber within each group was further dip-coated in a concentrated solution of La(dihed) dissolved in methanol. Methanol was removed by evaporation, leaving a coating of the selected metal β-diketonate polymer deposited over the top of the PDMS-coated fiber. PDMS fibers not coated with metal β-diketonate polymer served as controls.

Example 3

Explosive Analytes n-butyl nitrate was synthesized by the addition of n-butyl bromide to a slight excess of silver nitrate dissolved in acetonitrile [see, e.g., R. Boschan, R. T. Morrow, and R. W. van Dolah in: "The chemistry of nitrate esters", Chem. Rev. 55:483-510 (1955)]. After reacting overnight, silver bromide precipitate was filtered from the reaction mixture, oven dried, and weighed to provide an indication of reaction yield (98.3%). n-Butyl nitrate was isolated from the filtrate by extracting with methylene chloride, drying the methylene chloride with sodium sulfate, and removing the solvent by rotary evaporation. Crude product was purified by vacuum distillation. A product purity of 99+% was determined by gas chromatography/mass spectrometry (GC/MS) analysis. TNT was obtained commercially (Hercules, Wilmington, Del., USA) and was purified by repetitive recrystallization from ethanol. Triacetone triperoxide (TATP) was obtained commercially (AccuStandard, New Haven, Conn., USA) as a 100-ppm solution in acetonitrile. Before use, the acetonitrile solvent was exchanged for methylene chloride. N-Pentyl nitrate (n-amyl nitrate) was purchased (TCI America, Portland, Oreg., USA). 4-nitrotoluene (4-NT), 2,6-dinitrotoluene (2,6-DNT), and 2,3-dimethyl-2,3-dinitrobutane (DMDNB) were purchased (Sigma-Aldrich, St. Louis, Mo., USA).

Example 4

Stationary Phases Comprising Metal β-Diketonate Polymers

Control columns were prepared using a stationary phase consisting of CHROMOSORB-W® HP (100/120 mesh) (Supelco, Bellefonte, Pa., USA), a deactivated diatomaceous earth used as an inert support material, which was further loaded with 3% (w/w) SE-30 sorbent, a poly(dimethylsiloxane) elastomer (Supelco, Bellefonte, Pa., USA) prepared in methylene chloride solvent. Experimental stationary phases were prepared from a mixture of metal β-diketonate polymers dissolved or suspended in methanol and deposited onto the control material. Methanol solvent was removed by rotary evaporation, resulting in a 5% (w/w) loading of metal β-diketonate polymer in the experimental stationary phases.

Example 5

Sorbent-Packed Chromatographic Columns Comprising Metal β-Diketonate Polymers

Control sorbents were prepared as detailed in Example 4, which included a 3% loading (w/w) of SE-30 sorbent (Supelco, Bellefonte, Pa., USA) coated onto a support material comprised of CHROMOSORB-W® HP (100/120 mesh) (Supelco, Bellefonte, Pa., USA). Experimental sorbents were prepared by coating a 5% (w/w) loading of metal β-diketonate polymers onto the control sorbent. Sorbents were packed into stainless steel column blanks using silanized glass wool end plugs. A first column had an exemplary column dimension of (8 ft.×⅛ in.) O.D. (2.1 mm I.D.). A second column had an exemplary column dimension of (2 ft.×⅛ in.) O.D., which dimensions are not limited.

Example 6

Gas Chromatographic Analyses of Analytes

A Hewlett-Packard 5890 Series II gas chromatograph, modified with a packed column conversion kit was used. Helium carrier gas was delivered to the column at a flow rate of 25 mL/min through an injection port maintained at 200° C. Septum purge was adjusted to 1.5 mL/min. Columns were conditioned with helium flow at 210° C. overnight before connecting to the flame ionization detector. The detector temperature was held at 250° C. Sample injections were typically 1-2 µL of pentane or methylene chloride solvent that contained analytes of interest. Analyses were performed at various isothermal temperatures, or one of two temperature programs. Temperature programs started at 50° C. for 2 min before ramping at 10° C./min to a final temperature of either 180° C. or 200° C.; the final temperature was maintained for the remainder of the chromatographic run. Chromatographic traces were recorded on a Hewlett-Packard Model 3395 integrating recorder.

Example 7

Kováts Indices

Retention and Selectivity Assessment of Chromatographic Columns with Metal β-Diketonate Polymers Kováts indices were calculated from retention data (collected in triplicate) on both experimental and control columns for analytes introduced at defined temperatures. Data used to calculate Kováts indices were collected at 200° C. by bracketing TNT between n-alkanes on the control and metal β-diketonate columns. Adjusted retention times were calculated by using methane as a dead volume marker.

Example 8

Air Sample Collections of Analytes

Organics from a large-volume air sample were collected on a 60 g bed of XAD-2, a porous poly(styrene-divinylbenzene) support (Alltech Associates, Inc., Deerfield, Ill., USA), which was sandwiched between two polyurethane foam plugs. The sorbent bed had previously been exhaustively extracted with a series of solvents and dried in a vacuum oven. A vented ring compressor was used to pull $10^6$ L of air through the sorbent bed over a 68 hour period. Sorbed organics were subjected to Soxhlet extraction with pentane solvent. The resulting pentane extract was reduced in volume using a stream of dry nitrogen, split into two aliquots, one of which was fortified with TNT. Sample injections introduced to the gas chromatograph corresponded to an extrapolated 200 L of air. The fortified sample contained an extrapolated 47-ppt (v/v) TNT. Samples were analyzed on control and experimental columns prepared as detailed in Example 5.

While an exemplary embodiment of the present invention has been shown and described, it will be apparent to those skilled in the art that many changes and modifications may be made without departing from the invention in its true scope and broader aspects. The appended claims are therefore intended to cover all such changes and modifications as fall within the spirit and scope of the invention.

I claim:

1. A method for selective capture of gas-phase explosives or weaponized chemical agents, said method comprising the steps of:
    contacting a sensor having a gas-sampling structure that includes a metal β-diketonate polymer having at least one preselected coordinating ligand and a preselected R-group that provide a preselected selectivity for said gas-phase explosive or weaponized chemical agent with a sampling volume having a quantity of gas phase explosive or weaponized chemical agent therein, whereby said gas sampling structure selectively binds said gas-phase explosive or weaponized chemical agent.

2. The method of claim 1, wherein said metal β-diketonate polymer includes a preselected metal center selected from the group consisting of: La(III), Eu(III), Tb(III), Cu(II), Ni(II), and Zn(II), and combinations thereof.

3. The method of claim 1, wherein said metal β-diketonate polymer includes a preselected metal center that is a transition metal ion.

4. The method of claim 1, wherein said metal β-diketonate polymer includes a preselected metal center that is a lanthanide metal ion.

5. The method of claim 1, wherein the metal β-diketonate polymer includes an R-group that is optically active.

6. The method of claim 1, wherein the R-group is selected from the group consisting of: phenyl (—$C_6H_5$); methyl (—$CH_3$); ethyl (—$CH_2CH_3$); n-propyl; isopropyl; n-butyl; isobutyl; sec-butyl; tert-butyl, —$CF_3$; —$C_3F_7$, and combinations thereof.

7. The method of claim 1, wherein the metal β-diketonate polymer is selected from the group consisting of: Cu(dihed), Ni(dihed); Zn(dihed); La(dihed); Eu(dihed); Tb(dihed); and combinations thereof.

8. The method of claim 1, wherein the sensor includes a solid-phase microextraction (SPME) fiber.

9. The method of claim 1, wherein the the sensor includes a coating comprising said metal β-diketonate polymer.

10. The method of claim 1, wherein the sensor includes a filter surface.

11. The method of claim 10, wherein the filter surface comprises deactivated quartz fibers.

12. The method of claim 1, wherein the sensor includes a sorbent surface.

13. The method of claim 12, wherein said sorbent surface is comprised of said metal β-diketonate polymer.

14. The method of claim 1, further including the step of determining the identity of said gas-phase explosive or weaponized chemical agent.

15. A sensor for detection of gas-phase explosives or weaponized chemical agents, comprising:
    a metal β-diketonate polymer that includes a preselected metal center and at least one coordinating ligand comprising a preselected R-group that provide a preselected Lewis acidity and affinity for selective capture of said gas-phase explosives or weaponized chemical agents for determination thereof.

* * * * *